US009039718B2

(12) United States Patent
Rynerson

(10) Patent No.: US 9,039,718 B2
(45) Date of Patent: May 26, 2015

(54) METHOD AND DEVICE FOR TREATING AN OCULAR DISORDER

(75) Inventor: James M. Rynerson, Alvaton, KY (US)

(73) Assignee: Blephex, LLC, Lakeworth, FL (US)

( * ) Notice: Subject to any disclaimer, the term of this patent is extended or adjusted under 35 U.S.C. 154(b) by 311 days.

(21) Appl. No.: 13/556,729

(22) Filed: Jul. 24, 2012

(65) Prior Publication Data

US 2014/0031845 A1    Jan. 30, 2014

(51) Int. Cl.
*A61F 9/007* (2006.01)

(52) U.S. Cl.
CPC .................................. *A61F 9/00709* (2013.01)

(58) Field of Classification Search
CPC ............................. A61F 9/00; A61F 9/00709
USPC ................... 606/107, 162; 15/97.1; 128/898; 604/298–316; 601/72, 80, 139, 141, 601/142; 132/73.6, 75.8, 218
See application file for complete search history.

(56) References Cited

U.S. PATENT DOCUMENTS

| 4,778,457 | A |   | 10/1988 | York |
|---|---|---|---|---|
| 4,838,851 | A |   | 6/1989 | Shabo |
| 4,955,896 | A |   | 9/1990 | Freeman |
| 5,176,694 | A | * | 1/1993 | Price ............... 606/162 |
| 2006/0116355 | A1 |   | 6/2006 | Van Breen |
| 2007/0016255 | A1 | * | 1/2007 | Korb et al. ............ 607/1 |
| 2007/0060988 | A1 | * | 3/2007 | Grenon et al. .......... 607/96 |
| 2007/0231353 | A1 |   | 10/2007 | Gilbard et al. |
| 2010/0256552 | A1 | * | 10/2010 | Korb et al. ............ 604/20 |
| 2014/0221908 | A1 | * | 8/2014 | Sonsino et al. ......... 604/28 |

FOREIGN PATENT DOCUMENTS

| CN | 201692153 U | 1/2011 |
|---|---|---|
| JP | 10108801 A | 4/1998 |
| WO | 9633676 A1 | 10/1996 |
| WO | 2009066077 A1 | 5/2009 |
| WO | 2012092320 A2 | 7/2012 |
| WO | 2012092320 A3 | 7/2012 |

OTHER PUBLICATIONS

International Searching Authority, International Search Report and Written Opinion, International Application No. PCT/US2013/051850, mailed Oct. 14, 2013, 11 pp.
The Alger Company, Inc. "AlgerBrush II," available at <http://www.algercompany.com/download/ab_web/Algerbrush3_8.pdf>, accessed on Mar. 30, 2012, 1 page.

(Continued)

*Primary Examiner* — Todd Manahan
*Assistant Examiner* — Casey B Lewis
(74) *Attorney, Agent, or Firm* — Wood, Herron & Evans, LLP

(57) ABSTRACT

A method and apparatus for treating ocular disorders such as blepharitis, meibomitis, and dry eye syndrome. The method includes using an electromechanical device to move a swab relative to the eye to create cyclical movement that impacts debris present at the eyelid margin and effectively removes the debris from the eye to encourage healing and prevent further digression of the health of the eye. The apparatus is an electromechanical device that includes a mechanical drive unit operatively connected to a swab to create a precise relative movement of the swab to the eye to remove debris present therein.

17 Claims, 2 Drawing Sheets

(56) References Cited

OTHER PUBLICATIONS

1FORTHEMONEY, et al. "Blepharitis," available at <http://en.wikipedia.org/w/index.php?oldid=474399644>, accessed on Mar. 12, 2012, 6 pp.

The Alger Co., Inc. [online retrieved on Dec. 22, 2014]. Retrieved from the internet at <http://www.algercompany.com/brush/pdf-file/>, click on "Operating/Sterilization Procedures" then click on Algerbrush II Operating Instruction Rev. 32012 to retrieve pdf submitted herewith as "Algerbrush-II-Operating_instruct. 2012".

The Alger Co., Inc. [online retrieved on Dec. 22, 2014]. Retrieved from the internet at <http://www.algrecompany.com/brush/2013/01/02/the-algerbrush-ii-2/> Screen capture of page submitted herewith as "Algerbrush II Product Page."

Rhein Medical, Inc. [online retrieved on Jan. 8, 2015]. Retrieved form the internet at <http://www.rheinmedical.com/products-page/algerbrushes/08-13154-algerbrush-ii-chuch-2-5mm-round-fine-gruit-diamond-ball//> Screen capture of page submitted herewith as Algerbrush II chuck and round burr.

Ocusoft [online retrieved on Jan. 8, 2015]. Retrieved from the internet at <http://www.ocusoft.com/Foreign-body-Removal-AKGERBRUSH-II-CHUCK-P4666.aspx> Screen capture of page submitted herewith as Algerbrush II Chuck with bilobal fitting.

* cited by examiner

METHOD AND DEVICE FOR TREATING AN OCULAR DISORDER

TECHNICAL FIELD

The present invention relates generally to a method and apparatus for treating an ocular disorder, and more particularly, to treating eyelid margin disease.

BACKGROUND

Ocular disorders such as those relating to eyelid margin disease are particularly common pathological conditions of the ocular adenexa. By way of example, these disorders include blepharitis, meibomitis, and dry eye syndrome. Despite advances in ophthamology and medical treatments in general, the recommended treatments for these exemplary common ocular disorders has remained essentially unchanged for decades.

Historically, treatment of eyelid margin disease begins and ends with the patient. The patient first begins to notice symptoms including eyelid redness, flaking of skin on the eyelids, crusting and/or cysts at the eyelid margins, and a gritty sensation of the eye culminating in irritation, burning, and reduced vision. Should these symptoms remain unchanged or worsen, the patient routinely seeks the advice of an eye specialist, such as an ophthalmologist. After carefully considering the patients' medical history and investigating various possible causes, the specialist may prescribe a hygienic home treatment procedure for the patient to perform regularly in conjunction with antibiotics and/or topical steroids until the disease subsides.

The goal of the hygienic home treatment procedure is to remove debris, oil, and scurf that have collected along the eyelid margin during progression of the disorder. Removal of this debris is critical to both healing the eye and preventing a resurgence of the disorder. Without proper, regular removal of accumulated debris, such ocular disorders regularly worsen despite periodic treatments.

Hygienic home treatment of such ocular disorders is generally a two-step process. First, the patient softens the debris and scurf by applying a warm compress, diluted baby shampoo, or a specialized liquid solution to the eyelid margin. This first step is intended to prepare the debris for removal while preventing further irritation to the eye. Second, the patient attempts to remove the debris by physically scrubbing the eyelid margin, the base of the eyelashes, and the pores of the meibomian glands. This scrubbing is routinely attempted with either a generic cotton swab, a fingertip, or a scrub pad placed over the fingertip and applied against the eye. By cleaning debris and scurf free from the base of the eyelashes and unclogging the pores of the meibomian glands, the patient may improve the overall health of the eyelid margin; thereby reducing irritation, burning, and other symptoms related to the disorder.

Unfortunately for many patients, such hygienic home treatment is met with limited success due to the practical difficulties of cleaning one's own eye with an imprecise instrument such as a fingertip or cotton swab. For instance, many patients do not have the necessary dexterity to manipulate their fingertip or a cotton swab along the eyelid margin. Moreover, a shake, tremor, or poor near vision further complicate such self-treatment. Even for those capable of incorporating hygienic home treatment into their daily routine, many, if not most people, are wary of placing objects near their eyes to actively scrub along the eyelid margin. Given this anxiety, discomfort, and the inability to specifically target debris deposits, patients routinely fail to totally cleanse the margin of the eyelid, the base of the eyelashes, and the meibomian glands. While the attempted treatment may temporarily abate the patient's symptoms, subtle continuation of the disease often persists; thus permitting a low-grade inflammation to develop and, ultimately lead to chronic dry eye syndrome. Further, this treatment is typically required to be performed for the rest of the patient's life; thereby, creating a substantial hurdle to regular and effective compliance during hygienic home treatment.

Evidence suggests that medical costs associated with dry eye syndrome, often induced by ocular diseases such as blepharitis, are currently over 68 billion dollars each year. Many of these expenses are needlessly incurred due to the patients' failure to perform regular and effective treatments resulting in increased doctor visits, medications, and artificial tears. These expenses create a significant financial burden for insurance carriers, especially Medicare, which provides primary medical coverage for many individuals particularly prone to dry eye disease, such as the elderly.

There is a need for a method and apparatus for use in treating ocular disorders, such eyelid margin diseases, that addresses present challenges and characteristics such as those discussed above.

SUMMARY

One exemplary embodiment of the method according to this invention comprises using a swab operably connected to an electromechanical device to treat an ocular disorder. The disorders to be treated via this method result in a build-up of a removable debris on the eye. The swab, which moves relative to the electromechanical device, contacts the portion of the eye that includes the removable debris. Thereby, the swab impacts the debris to remove the debris from the eye. Removing the debris further includes at least one of breaking the debris free of the eyelid margin, scrubbing the eyelid margin, exfoliating the eyelid margin, buffing the eyelid margin, or un-roofing the meibomian gland.

In one aspect, the swab is positioned near the eyeball along the eyelid margin to target the debris with the swab. The eyelid margin is accessed with the swab without the aid of a magnification device and without lifting the eyelid margin.

In another aspect, effecting movement of the swab relative to the electromechanical device includes at least one of rotating, vibrating, or reciprocating the swab. Furthermore, the movement of the swab may be set to a desirable speed.

Treating the eye for the ocular disorder may include repeating the effecting movement, the contacting the portion of the eye, and impacting the debris with the swab to remove the debris after periodic intervals until the ocular disorder is sufficiently remedied.

In another exemplary embodiment, a device for the removal of debris from the eye during the treatment of the ocular disorder comprises a swab having a tip portion and a base portion. The tip portion is of a sufficient size to access debris on the eye. The device also includes a rigid member and a mechanical drive unit. As such, the rigid member and the swab extend from an instrument. The rigid member has a distal end portion and a proximal end portion such that the distal end portion is affixed to the base portion of the swab and the proximal end portion is secured to the mechanical drive unit, which also includes a body. The mechanical drive unit operably moves the swab relative to the body facilitating removal of the debris from on the eye.

In one aspect, the swab is a generally egg-shaped sponge having an approximate length of two millimeters and a width of one millimeter. Affixed to the sponge, the rigid member is a plastic material that is formed onto the distal end portion of the rigid member.

In yet another aspect, the mechanical drive unit includes an electric motor, a chuck, and a control switch. The chuck projects from the body of the mechanical drive unit and is operably connected to the electric motor. Also, the control switch is operably coupled to the electric motor. With respect to the rigid member, the proximal end portion of the rigid member is removably secured to the chuck. In addition, the device is handheld and includes an electric power source operably coupled to the mechanical drive unit, the electric power source being a battery.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
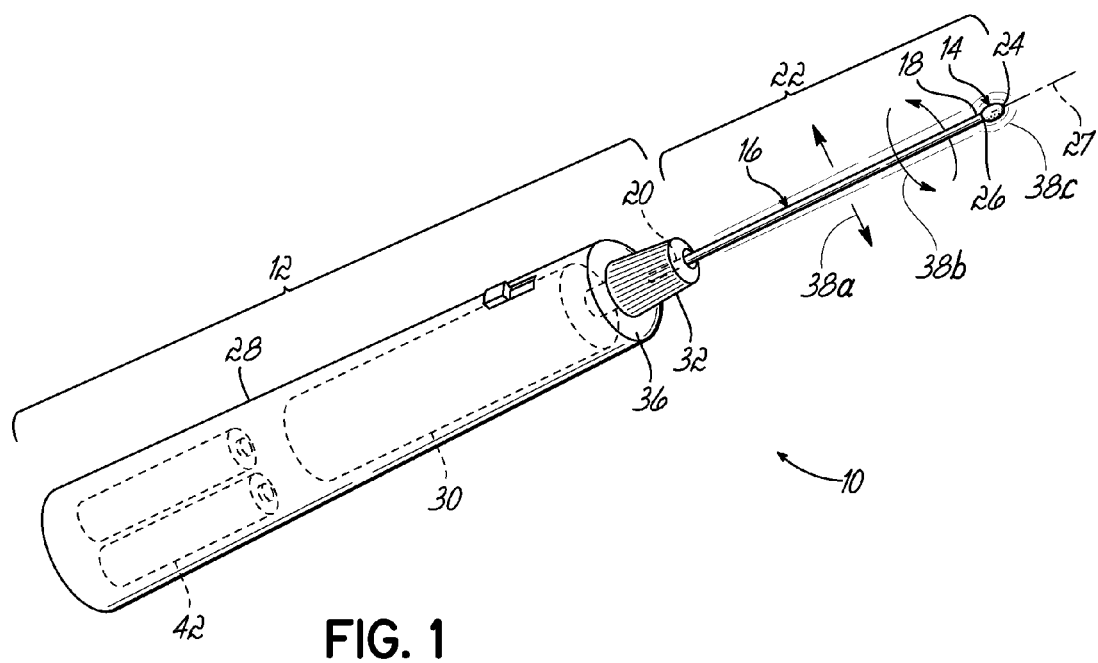
FIG. 1 is a perspective drawing of one embodiment of the device.
Figure 2A:
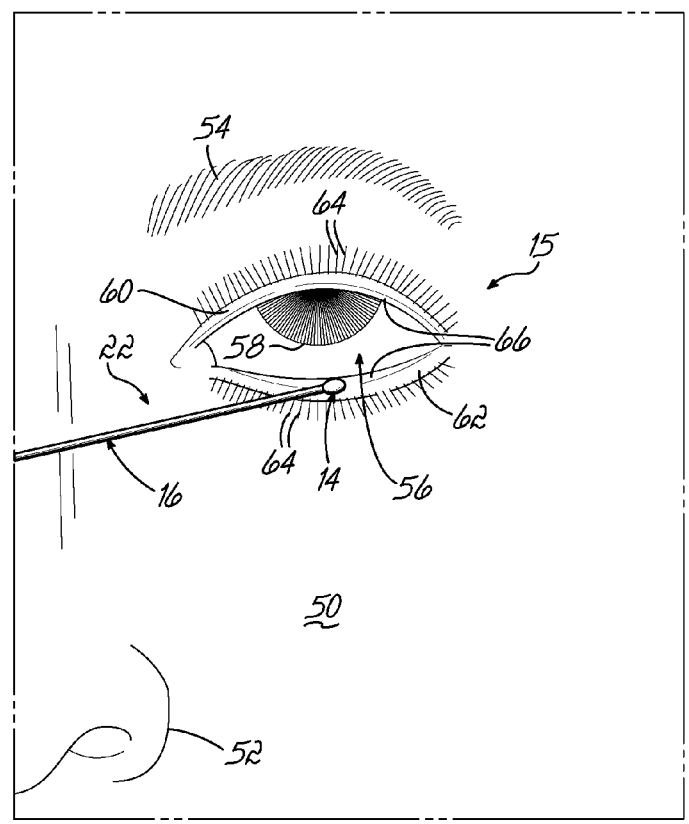
FIG. 2A is a drawing of the device of FIG. 1 treating a lower eyelid margin of an eye.
Figure 2B:
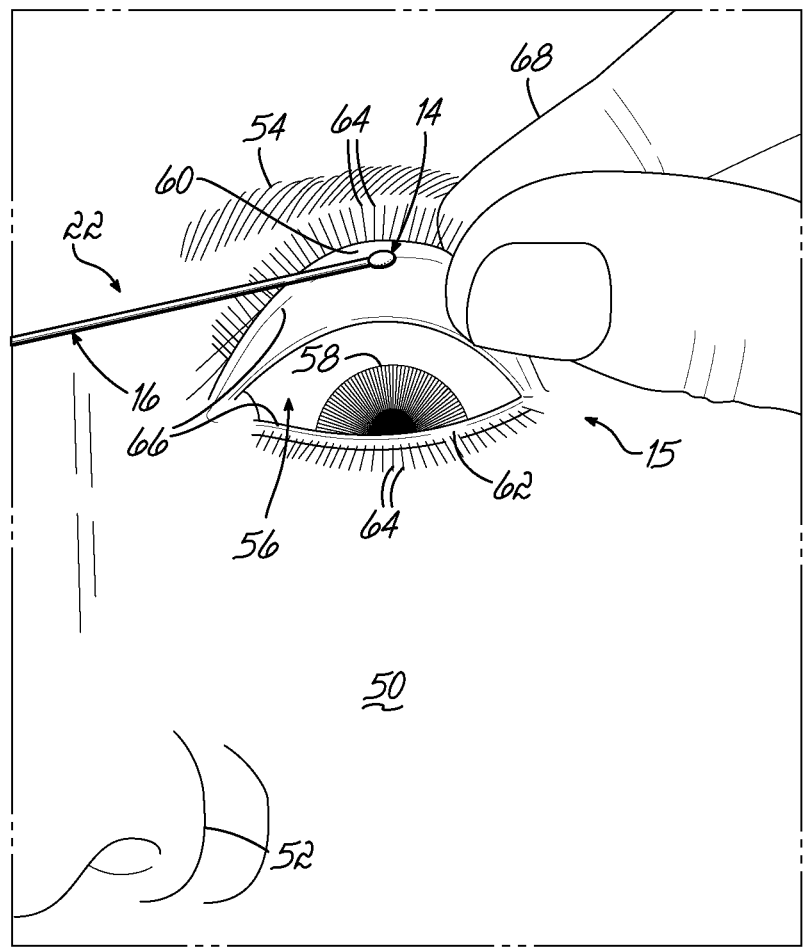
FIG. 2B is a drawing of the device of FIG. 1 treating a upper eyelid margin of an eye.

With reference to FIG. 1, an embodiment of the device 10 for treating an ocular disorder, particularly with respect to eyelid margin diseases, includes a mechanical drive unit 12 which operably moves a swab 14 to facilitate removal of debris from an eye 15 (see FIGS. 2A-2B). The swab 14 is connected to a rigid member 16 having both a distal end portion 18 and a proximal end portion 20. The swab 14 is affixed to the distal end portion 18 of the rigid member 16 to create an instrument 22, which may be secured to the mechanical drive unit 12. As shown in FIG. 1, the proximal end portion 20 is removably secured to the mechanical drive unit 12 in order to transmit motion from the mechanical drive unit 12, through the rigid member 16, and to the swab 14. It will be appreciated that any known method may be used to removably secure the instrument 22 to the mechanical drive unit 12. Moreover, it will also be appreciated that device 10 is not intended to be limited to the instrument 22 being removably secured to the mechanical drive unit 12. For instance, in another embodiment, the rigid member 16 may be either permanently secured or removably secured to either one of the swab 14 and/or the mechanical drive unit 12.

In one aspect of the instrument 22, the swab 14 includes a tip portion 24 and a base portion 26. While the swab 14 may be of a size sufficient to access debris on the eye 15 as shown in FIGS. 1-2B, at least the tip portion 24 is of a size sufficient to access debris on the eye 15. For instance, the swab 14 has an approximate length between 1.0-3.0 millimeters and an approximate width of between 0.5-1.5 millimeters. More particularly, the swab 14 has an approximate length of 2 millimeters and an approximate width of 1 millimeter. It will be appreciated that the swab 14 may be manufactured of any material suitable for contacting the eye 15 without harming the eye 15. However, as shown in the embodiment of FIG. 1, the swab 14 is a sponge. As described herein, "sponge" broadly refers to any material that is soft, porous, and resilient. Particularly, the swab 14 is a medical grade sponge or a surgical grade sponge capable of removing debris from on the eye 15 without harming the eye 15. As shown in the exemplary embodiment of FIGS. 1-2B, the swab 14 is a methyl cellulose sponge. It will be appreciated; however, that similar materials capable of removing debris from on the eye 15 without harming the eye 15 are readily apparent and may also be used.

In another aspect of the instrument 22, the rigid member 16 is a plastic, cylindrical shaft including a central axis 27. The shaft extends along the central axis 27 between the mechanical drive unit 12 and the swab 14. The rigid member 16 is sufficiently rigid to effectively transmit motion from the mechanical drive unit 12 to the swab 14. As shown in FIG. 1, the swab 14 is permanently affixed to the distal end portion 18 by forming the base portion 26 to the rigid member 16 during manufacturing. However, it will be appreciated that any known method of affixing the swab 14 to the rigid member 16 may be used. In an exemplary embodiment, any material or shaft shape may be used so long as the rigid member 16 is rigid enough to transmit sufficient motion from the mechanical drive unit 12 to the swab 14 in order to remove debris from on the eye 15.

Furthermore, the mechanical drive unit 12 includes a body 28, an electric motor 30, a chuck 32, and a control switch 34. As such, the device 10 is electromechanical in nature. In an exemplary embodiment, the electric motor 30, the chuck 32, and the control switch 34 are integrated into the body 28 so that the electromechanical device 10 is configured to be handheld as shown in FIG. 1. However, the electromechanical device 10 is not intended to be limited to a handheld configuration, and it will be appreciated that other configurations of the device 10 are readily apparent.

According to the present embodiment, the electric motor 30 is positioned within the body 28. The chuck 32 is operably connected to the electric motor 30 at a forward end portion 36 of the body 28. The proximal end portion 20 of the rigid member 16 is removably secured to the chuck 32. As described herein, the chuck 32 is generally any element capable of removably securing the rigid member 16 to the mechanical drive unit 12. As such, the chuck 32 may be tightened or loosened to respectively secure or remove the instrument 22 to the chuck 32. Thereby, the operable connection of the electric motor 30 transmits a movement 38 through the chuck 32 to the instrument 22. The movement 38 is any motion relative to the mechanical drive unit 12 or, more particularly, to the body 28, that creates relative motion to the debris on the eye 15 such that upon contacting the debris with the swab 14, the debris is removed. As shown, the movement 38 may include, but is not limited to, a reciprocating movement 38a, a rotating movement 38b, or a vibrating movement 38c. The reciprocating movement 38a may be either along the central axis 27 of the rigid member 16 or orthogonal to the central axis 27 of the rigid member 16. In addition, the speed of the movement 28 of the swab 14 is any speed sufficient to remove debris from on the eye 15. It will be appreciated that the speed discussed herein collectively refers to both relative speed of the swab 14 and the frequency of the movement 38 of the swab 14. For instance, the frequency may range from sonic frequencies to ultrasonic frequencies. Furthermore, the speed of the swab 14 may be variable or otherwise selectable such that an operator of the device 10 may select a desirable speed or a forward or reverse direction via the control switch 34.

Moreover, the control switch 34 is operably connected to the electric motor 30 and an electric power source 42 to power the device 10 on and off. In an exemplary embodiment, the electric power source 42 is a battery power source 42 contained within the body 28. The battery power source 42 may be either disposable or rechargeable. The electric power source 42 operably provides electrical power to the electric motor 30, which the operator controls via the control switch 34. It will be appreciated that any known control switch 34 or plurality of control switches 34 may be configured to power the device 10 on and off.

Furthermore, it will be appreciated that the device 10 may be manufactured from various materials suited to specific environments of use. For instance, operators within the professional clinic setting may desire a durable, reusable mechanical drive unit 12 and single-use instruments 22. Some examples of such a professional mechanical drive unit 12 is an Algerbrush I, an Algerbrush II, or similar medical device. However, operators within the home treatment setting may desire the device 10 to be generally disposable and single-use.

With respect to FIGS. 2A and 2B, the device 10 is used in a method for treating ocular disorders of the eye 15. For purposes of describing the environment in which this method occurs, FIGS. 2A and 2B generally show a portion of a face 50 having a nose 52, an eyebrow 54, and the eye 15. The eye 15 described herein generally includes, but is not limited to, an eyeball 56 including a cornea 58, an upper eyelid margin 60, a lower eyelid margin 62, and a plurality of eyelashes 64. In the exemplary embodiment, the device 10 is the swab 14 operably connected to the mechanical drive unit 12 thereby creating the electromechanical device 10 for use in removing debris deposited on at least one of either the upper eyelid margin 60 or the lower eyelid margin 62.

As shown in FIG. 1, the electromechanical device 10 is powered on and may be set to a desirable speed by the operator; thereby, the operator effects movement of the swab 14 relative to the electromechanical device 10. Such movement may include, but is not limited to, reciprocating the swab 14 as shown by arrows 38a, rotating the swab 14 as shown by arrow 38b, and/or vibrating the swab 14 as shown by lines 38c. The swab 14 is positioned near the eyeball 56 and along either one of the upper or lower eyelid margins 60, 62 for treatment. In the exemplary embodiment as shown in FIGS. 2A and 2B, the swab 14 moves with constant movement relative to the electromechanical device 10 while near the eyeball 56. Alternatively, it may be desirable to vary the movement of the swab 14 relative to the electromechanical device 10 such that the operator has greater control of treating the ocular disorder.

In an exemplary embodiment, the operator preferably targets the debris present on the eye 15 with the swab 14 of the electromechanical device 10. The debris may be targeted by visually inspecting the eye 15 with or without the aid of a magnification device. Once the debris is targeted, the swab 14 contacts the portion of the eye 15 that includes the debris. For purposes of treating the ocular disorder, the debris may be removably attached on either the upper and lower eyelid margins 60, 62 the plurality of eyelashes 64, or between the eyelashes 64 and the inner edge of the eyelid margins, 60, 62. Thereby, upon contacting the portion of the eye 15 with the debris, the swab 14 impacts the debris to remove the debris from the eye 15. Furthermore, a liquid solution configured to loosen the debris may be absorbed within the swab 14 to further aid in removing the debris from the eye 15 and/or minimizing irritation to the eye 15. It will be appreciated that any liquid solution sufficiently capable of loosening the debris to further aid in removing the debris may be so used.

The electromechanical device 10 operably drives the swab 14 to break the debris free from either of the upper or lower eyelid margins 60, 62. Further treatment may be performed to enhance the effects of the debris removal by helping to improve healing and reducing further infection of the eye 15. Such treatment may include scrubbing, exfoliating, or buffing the eyelid margin or un-roofing a meibomian gland 66 with the swab 14.

In another aspect, the cornea 58 of the eye 15 is directed away from the position of the swab 14 to minimize contacting the swab 14 to the cornea 58 during treatment. As shown in FIG. 2A, while treating the lower eyelid margin 62, the eyeball 56 directs the cornea 58 upward, thereby bringing the cornea 58 closer to the upper eyelid margin 60 than the lower eyelid margin 62. However, as shown in FIG. 2B, while treating the upper eyelid margin 60, the eyeball 56 directs the cornea 58 downward, thereby being closer to the lower eyelid margin 62 than the upper eyelid margin 60.

As shown in FIG. 2A, accessing the portion of the eye 15 with the debris, such as the upper or lower eyelid margins 60, 62, may be accomplished without further moving or lifting other portions of the eye 15. However, as shown in FIG. 2B, if accessing the portion of the eye 15 with the debris is difficult, the operator may use a hand 68, or similar gripping device, to move or lift a portion of the eye 15, such as lifting the upper or lower eyelid margin 60, 62 from against the eyeball 56, to improve access to the debris. Such lifting may be particularly beneficial for improving access to the meibomian gland 66. It will be appreciated that, in order to improve access to the debris, any portion of the eye 15 may be moved or lifted regardless of which eyelid margins 60, 62 are being treated. FIGS. 2A and 2B are merely exemplary embodiments showing both non-assisted access and assisted access of the swab 14 to the eye 15 respectively.

Furthermore, the method of treating the ocular disorder may be repeated as directed by a physician or patient in order to sufficiently remedy the disorder. For instance, in the case of physician directed treatment, the physician may direct the patient to visit the physician in periodic intervals for treating the ocular disorder with the electromechanical device 10. More specifically, the physician directs the patient to visit the physician in periodic monthly or weekly intervals so that the physician may treat the patient. In the exemplary embodiment, periodic intervals are treatments with the electromechanical device 10 once every month. It will be appreciated that any periodic interval of repeating the method of treating the ocular disorder with the electromechanical device 10 may be so used.

Alternatively, in the case of home treatment by the patient, the patient may treat his or her own ocular disorder with the electromechanical device 10 in periodic intervals. However, according to the exemplary embodiment, the physician repeats the method of treating the ocular disorder in periodic intervals with the electromechanical device 10 and the patient also treats the ocular disorder in between physician treatments using traditional treatments. This method of treating the ocular disorder with the electromechanical device 10 in treatments occurring in periodic intervals achieves superior removal of the debris compared to traditional treatments, because the periodic intervals act as reminders to the patient. Thus, the patient is less likely to forget to treat the ocular disorders once symptoms begin to subside, which may result in a resurgence of the disorder. However, the traditional treatments, despite being less effective, may be performed regularly by the patient to further treat the ocular disorder in conjunction with physician treatments with the electromechanical device 10.

In any case, the physician or patient treats the ocular disorder until the ocular disorder is sufficiently healed and thereafter to prevent a recurrence of the disorder. It will be appreciated that sufficiently healed refers to the dissipation of inflammation and/or discomfort related to the debris within the eye 15 at which time the treatments by the physician may decrease in frequency, but may continue in periodic intervals during home treatment by the patient. In the event that the inflammation, discomfort, or debris worsens, the method of treating the ocular disorder may resume as the physician or patient desires. However, the treatment may be required in periodic intervals throughout the remainder of the patient's life.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A method of treating an eye for an ocular disorder with a swab operably connected to an electromechanical device, wherein the eye has an eyelid margin and includes a removable debris, the method comprising;
    effecting movement of the swab relative to the electromechanical device, the swab having at least a portion thereof configured to access an inner edge portion of the eyelid margin;
    while the swab is being moved by the electromechanical device, contacting a portion of the eye between the eyelashes and the inner edge of the eyelid margin that includes the removable debris with the swab thereby impacting the debris with the swab to remove debris from the eye.

2. The method of claim 1 wherein the eye has a meibomian gland and removing debris further includes at least one of:
    scrubbing the eyelid margin;
    exfoliating the eyelid margin;
    buffing the eyelid margin;
    un-roofing the meibomian gland; or
    breaking the debris free of the eyelid margin.

3. The method of claim 1 wherein the eye has an eyeball and further includes accessing the eyelid margin for contacting the swab to the debris without lifting the eyelid margin from the eye.

4. The method of claim 1 wherein the eye has an eyeball and further includes:
    positioning the swab near the eyeball along the eyelid margin; and
    targeting the debris with the swab.

5. The method of claim 1 further including viewing the eye and the debris without the aid of a magnification device.

6. The method of claim 1 wherein the movement of the swab is at least one of rotating the swab, vibrating the swab, or reciprocating the swab.

7. The method of claim 1 wherein effecting movement of the swab further includes setting the movement of the swab to a desirable speed sufficient to remove the debris from the eye.

8. The method of claim 1 further including repeating the effecting movement, the contacting the portion of the eye, and impacting the debris with the swab to remove the debris process of claim 1 after periodic intervals until the ocular disorder is sufficiently remedied.

9. The method of claim 1 wherein the swab is connected to a rigid member having a proximal end portion, the method further comprising:
    securing the proximal end portion of the rigid member to the electromechanical device; and
    removing the proximal end portion of the rigid member from the electromechanical device.

10. The method of claim 9 further comprising:
    removing the proximal end portion of the rigid member after a single use of the swab; and
    repeating the securing and removing of another proximal end portion of another rigid member.

11. The method of claim 1 wherein the swab is a medical grade sponge for accessing the eyelid margin.

12. The method of claim 1 wherein the swab has a length and a width, the length being between 1.0 millimeter and 2.0 millimeters and the width being between 0.5 millimeters and 1.5 millimeters for accessing the inner edge portion of the eyelid margin.

13. The method of claim 1 wherein the swab is generally egg-shaped having an approximate length of 2 mm and an approximate width of 1 mm for accessing the inner edge portion of the eyelid margin.

14. The method of claim 1 further comprising:
    accessing at least an inner edge portion of the eyelid margin with swab.

15. The method of claim 14 further comprising:
    contacting the inner edge portion of the eyelid margin with the swab.

16. The method of claim 1 wherein the movement of the swab is rotating the swab.

17. A method of treating an eye for an ocular disorder with a swab operably connected to an electromechanical device, wherein the eye has an eyelid margin and includes a removable debris, the method comprising;
    effecting movement of the swab relative to the electromechanical device;
    while the swab is being moved by the electromechanical device, contacting at least an inner edge portion of the eyelid margin that includes the removable debris with the swab thereby impacting the debris with the swab to remove debris from the eye.

* * * * *

UNITED STATES PATENT AND TRADEMARK OFFICE
CERTIFICATE OF CORRECTION

PATENT NO. : 9,039,718 B2  
APPLICATION NO. : 13/556729  
DATED : May 26, 2015  
INVENTOR(S) : James M. Rynerson It is certified that error appears in the above-identified patent and that said Letters Patent is hereby corrected as shown below:

In the specification,

| | | |
|---|---|---|
| Column 1, line approximately 7, "disorder, and more" | should read | --disorder and, more-- |
| Column 1, line approximately 28, " patients' medical" | should read | --patient's medical-- |
| Column 2, lines approximately 14-15, "patients' failure" | should read | --patient's failure-- |
| Column 2, line approximately 22, "such eyelid" | should read | --such as eyelid-- |
| Column 4, line approximately 7, "appreciated; however" | should read | --appreciated, however-- |
| Column 5, line approximately 61, "margins, 60, 62" | should read | --margins 60, 62.-- |
| Column 7, line approximately 26, "departures may be from" | should read | --departures may be made from-- |

In the claims,

| | | |
|---|---|---|
| CLAIM 1, column 7, line 33, "method comprising;" | should read | --method comprising:-- |
| CLAIM 12, column 8, line 30, "0.5 millimeters" | should read | --0.5 millimeter-- |
| CLAIM 14, column 8, line 39, "with swab." | should read | --with the swab.-- |
| CLAIM 17, column 8, line 48, "method comprising;" | should read | --method comprising:-- |

Signed and Sealed this  
Twenty-second Day of December, 2015

Michelle K. Lee  
*Director of the United States Patent and Trademark Office*

Page 1 of 1